(12) United States Patent
Hull et al.

(10) Patent No.: US 9,658,297 B2
(45) Date of Patent: May 23, 2017

(54) MAGNETIC PERMEABILITY MEASUREMENT OF FERROMAGNETIC WIRES

(71) Applicant: The Boeing Company, Chicago, IL (US)

(72) Inventors: John R. Hull, Sammamish, WA (US); Robert James Miller, Fall City, WA (US)

(73) Assignee: The Boeing Company, Chicago, IL (US)

( * ) Notice: Subject to any disclaimer, the term of this patent is extended or adjusted under 35 U.S.C. 154(b) by 198 days.

(21) Appl. No.: 14/589,343

(22) Filed: Jan. 5, 2015

(65) Prior Publication Data

US 2016/0195495 A1    Jul. 7, 2016

(51) Int. Cl.
*G01R 33/02* (2006.01)
*G01R 33/038* (2006.01)
*G01N 27/82* (2006.01)

(52) U.S. Cl.
CPC ......... *G01R 33/02* (2013.01); *G01R 33/0385* (2013.01); *G01N 27/825* (2013.01)

(58) Field of Classification Search
CPC .... G01R 31/02; G01R 31/021; G01R 15/186; G01N 27/72; G01N 27/82; G01N 27/825
See application file for complete search history.

(56) References Cited

U.S. PATENT DOCUMENTS

| | | | | |
|---|---|---|---|---|
| 4,234,863 A * | 11/1980 | Shumway | ................ | G01R 1/06 324/127 |
| 4,407,682 A * | 10/1983 | Sawa | ...................... | B21C 51/00 148/509 |
| 4,427,940 A * | 1/1984 | Hirama | ................... | B66B 7/123 324/206 |
| 8,154,279 B1 * | 4/2012 | Zamanzadeh | ...... | G01R 33/1223 324/228 |
| 2005/0061081 A1 * | 3/2005 | Butler | ....................... | G01L 1/10 73/778 |

* cited by examiner

*Primary Examiner* — Jermele M Hollington
*Assistant Examiner* — Dustin Dickinson
(74) *Attorney, Agent, or Firm* — Duft Bornsen & Fettig, LLP

(57) ABSTRACT

Embodiments described herein provide magnetic permeability measurements of ferromagnetic wires. In one embodiment, an apparatus comprises a non-magnetic wire retainer having a circular groove that holds a ferromagnetic wire for measurement. The apparatus further comprises a magnetic field generator proximate to the non-magnetic wire retainer that provides a substantially uniform magnetic field along a circumference of the circular groove. The apparatus further comprises a force sensor mechanically coupled to the magnetic field generator that measures an attractive force between the magnetic field generator and the ferromagnetic wire for determining the magnetic permeability of the ferromagnetic wire.

10 Claims, 7 Drawing Sheets

MAGNETIC PERMEABILITY MEASUREMENT OF FERROMAGNETIC WIRES

FIELD

This disclosure relates to the field of wire testing, and in particular, to testing ferromagnetic wires.

BACKGROUND

Induction heating processes may use ferromagnetic wires that heat up when exposed to alternating magnetic fields. For example, blankets that include ferromagnetic wires can be wrapped around thermoset composite parts. The blanket is then exposed to an alternating magnetic field, which induces alternating currents within the wires. The wires are heated due to $I^2R$ and magnetic hysteretic losses.

The magnetic permeability of the wires is one factor that can affect the heating performance of the blanket. Wires that have different magnetic permeability will exhibit different heating profiles within the same alternating magnetic field. This may cause hot spots in the blankets or temperature variations from one blanket to the next, which can cause problems in manufacturing processes that utilize ferromagnetic wires for induction heating. Generally, the magnetic permeability of ferromagnetic wires can change substantially during the manufacturing of the wires, with small changes in the composition of the wires and changes in how the wire-drawing process alters the grain size and orientation of the grains being some of the factors.

With the possibility that slight changes in the manufacturing process for the wires can produce substantial changes in the magnetic permeability of the wires, it is important to quickly and efficiently determine the magnetic permeability of samples of ferromagnetic wires that will be used to fabricate induction heating products, such as induction heating blankets.

SUMMARY

Embodiments described herein provide magnetic permeability measurements of ferromagnetic wires based on the attractive force between a magnetic field generator and a sample of a ferromagnetic wire. With similar testing conditions (e.g., similar distances between the samples and the magnetic field generator, similar temperatures during measurements, etc.), the variations in the attractive force calculated from one sample to the next indicate differences in the magnetic permeability of the samples.

One embodiment is an apparatus for measuring a magnetic permeability of a ferromagnetic wire. The apparatus comprises a non-magnetic wire retainer having a circular groove that is configured to retain the ferromagnetic wire for measurement. The apparatus further comprises a magnetic field generator proximate to the non-magnetic wire retainer that is configured to provide a substantially uniform magnetic field along a circumference of the circular groove. The apparatus further comprises a force sensor coupled to the magnetic field generator that is configured to measure an attractive force between the magnetic field generator and the ferromagnetic wire for determining the magnetic permeability of the ferromagnetic wire.

Another embodiment is a method for measuring a magnetic permeability of a ferromagnetic wire. The method comprises retaining the ferromagnetic wire within a circular groove of a non-magnetic wire retainer, and applying a substantially uniform magnetic field along a circumference of the circular groove utilizing a magnetic field generator. The method further comprises measuring an attractive force between the magnetic field generator and the ferromagnetic wire for determining the magnetic permeability of the ferromagnetic wire.

Another embodiment is an apparatus for in-line measurement of changes in a magnetic permeability along a length of ferromagnetic wire. The apparatus comprises a first and second wire roller, where the first wire roller is configured to direct the length of ferromagnetic wire under tension to the second wire roller for the in-line measurement. The apparatus further comprises a magnetic field generator disposed between the first and second wire roller that is proximate to the ferromagnetic wire under tension. The apparatus further comprises a force sensor coupled to the magnetic field generator that is configured to measure attractive forces between the magnetic field generator and the ferromagnetic wire under tension for determining changes in the magnetic permeability along the length of ferromagnetic wire.

The above summary provides a basic understanding of some aspects of the specification. This summary is not an extensive overview of the specification. It is intended to neither identify key or critical elements of the specification nor delineate any scope of the particular embodiments of the specification, or any scope of the claims. Its sole purpose is to present some concepts of the specification in a simplified form as a prelude to the more detailed description that is presented later.

DESCRIPTION OF THE DRAWINGS

Some embodiments are now described, by way of example only, and with reference to the accompanying drawings. The same reference number represents the same element or the same type of element on all drawings.

DESCRIPTION

Figure 1:
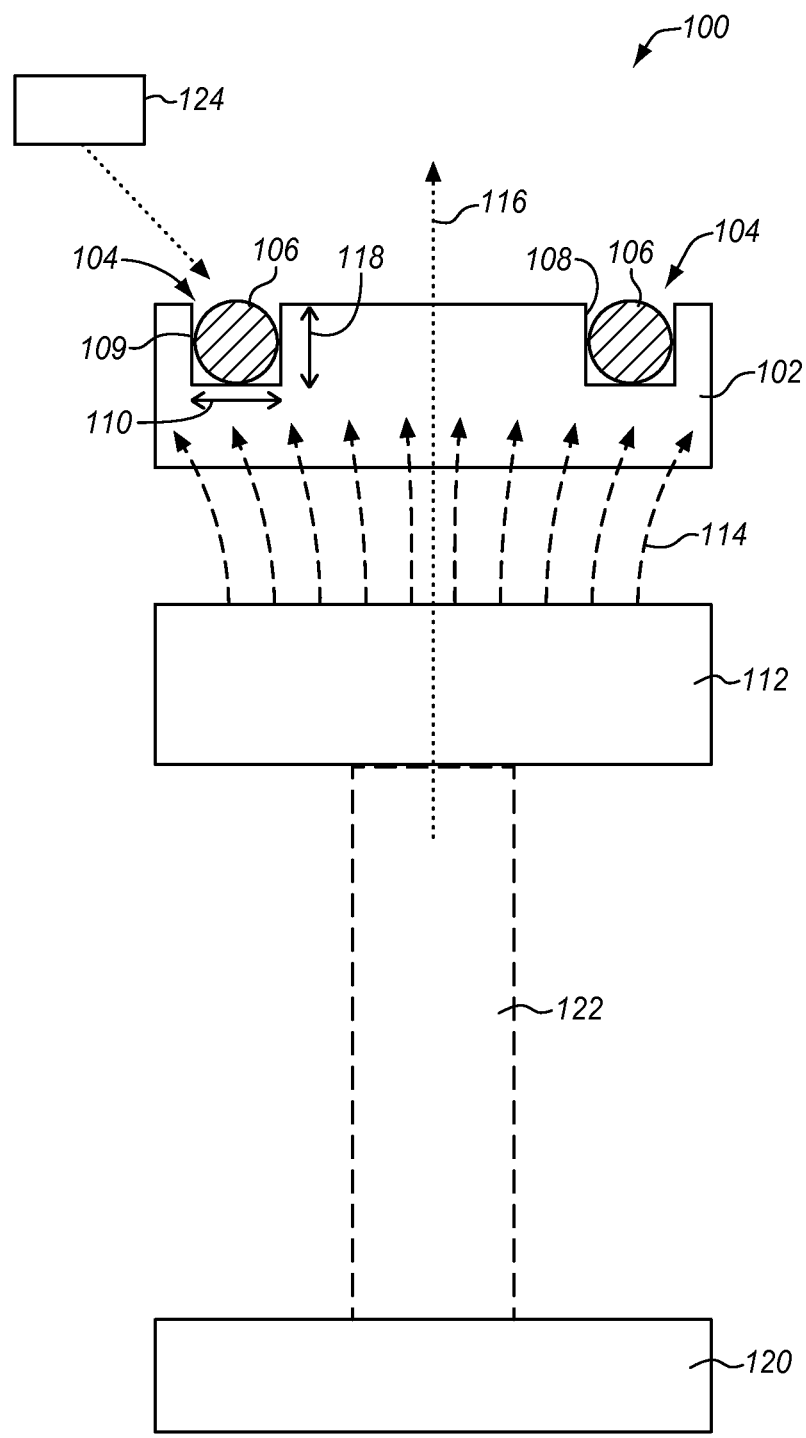
FIG. 1 illustrates a system for measuring a magnetic permeability of a ferromagnetic wire in an exemplary embodiment.

The figures and the following description illustrate specific exemplary embodiments. It will thus be appreciated that those skilled in the art will be able to devise various arrangements that, although not explicitly described or shown herein, embody the principles of the embodiments and are included within the scope of the embodiments.

Furthermore, any examples described herein are intended to aid in understanding the principles of the embodiments, and are to be construed as being without limitation to such specifically recited examples and conditions. As a result, the inventive concept(s) is not limited to the specific embodiments or examples described below, but by the claims and their equivalents.

Magnetic permeability is the ability of a material to support the formation of a magnetic field within itself in response to an applied magnetic field (B). In the International System of Units (SI), magnetic permeability is measured in henries (H) per meter (m) ($H \cdot m^{-1}$). Magnetic permeability is typically represented by the Greek letter $\mu$. Sometimes materials are described both in terms of their magnetic permeability ($\mu$) and their relative permeability ($\mu/\mu_0$), where $\mu_0$ is the permeability of free space ($4\pi \times 10^{-7}$ $H \cdot m^{-1}$). By this definition, the relative permeability of a vacuum is 1, while the relative permeability of Iron is about 200,000. Thus, an Iron bar is about 200,000 times more effective in supporting the formation of an internal magnetic field than is possible in a vacuum.

Iron is one example of a ferromagnetic material, with other examples being Nickel and Cobalt. Alloys of Iron, Nickel, and Cobalt are often ferromagnetic as well. Ferromagnetic materials such as Iron, Nickel, and Cobalt can be useful in induction heating systems, which utilize an alternating magnetic field to transfer energy to a target. In an induction heating system, an alternating magnetic field transfers energy to a conductive metal, which self-heats due to the induced currents in the metal. When the metal is also ferromagnetic, additional self-heating is produced in the metal due to magnetic hysteresis, which is the work needed to re-orient the magnetic dipoles in the material in the presence of an external magnetic field. Thus, materials such as Iron that have a relatively high magnetic permeability (e.g., 200,000) self-heat more effectively than Aluminum, which has a relatively low magnetic permeability (e.g., about 1).

In induction heating blankets, for example, changes in the magnetic permeability of the heating wires in the blankets modify how effective the heating wires will self-heat. Sometimes this can be desirable, and at other times, not. For instance, heating wires that decrease in magnetic permeability at a target temperature can be useful in controlling the final temperature of the induction heating blanket. As the heating wires heat up in the presence of the alternating magnetic field, the magnetic permeability decreases, which reduces the self-heating in the heating wires. However, changes in the magnetic permeability of the heating wires from one blanket to the next may cause problems in manufacturing processes that expect the blankets to exhibit a well-defined heating profile. Further, differences in the magnetic permeability of the heating wires from one blanket to the next at a particular wire temperature may result in some blankets becoming hotter than expected and other blankets becoming colder than expected when exposed to similar alternating magnetic field strengths. This variation is undesirable because it may impact the manufacturing quality of thermoset or thermo-cured parts that utilize inductive heating blankets during the manufacturing process.

FIG. 1 illustrates a system 100 for measuring a magnetic permeability of a ferromagnetic wire in an exemplary embodiment. In this embodiment, system 100 includes a wire retainer 102 that is proximate to a magnetic field generator 112. Wire retainer 102 is formed from a non-magnetic material. Some examples of non-magnetic materials that wire retainer 102 may be formed from include fiberglass, aluminum, plastic, aerogels, etc.

Figure 2:
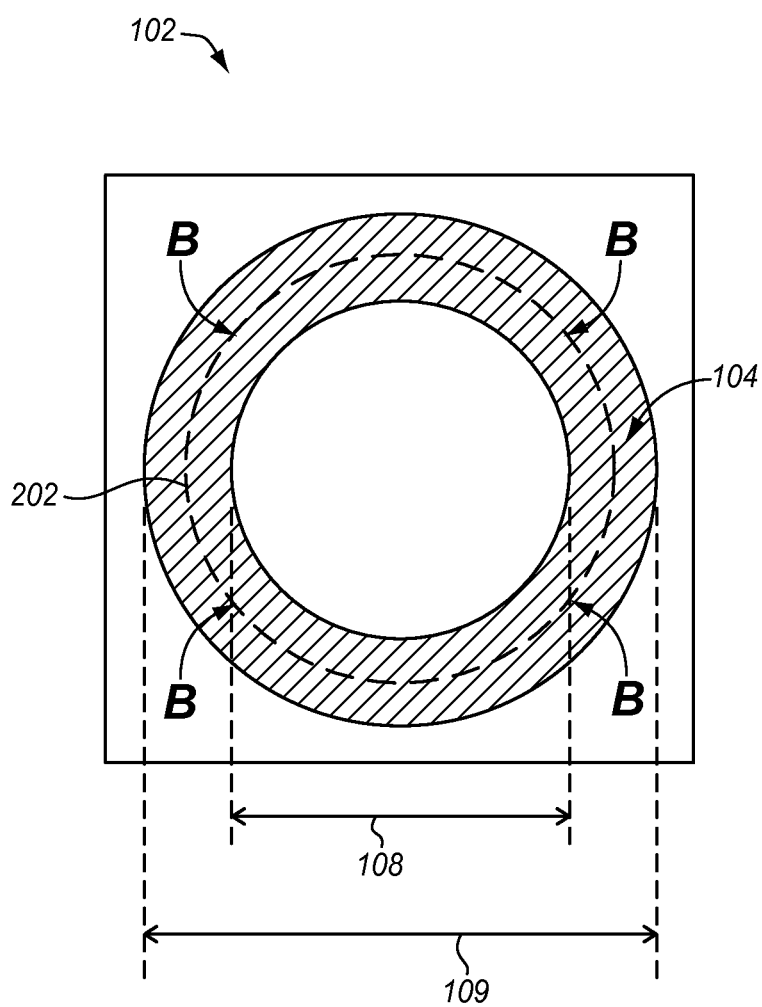
FIG. 2 illustrates a top view of the wire retainer of FIG. 1 in an exemplary embodiment.

In this embodiment, wire retainer 102 includes a circular groove 104 which retains a sample of ferromagnetic wire 106. FIG. 1 illustrates a cross-sectional view of wire retainer 102, which obscures that groove 104 is circular. However, this feature is more clearly visible in FIG. 2. FIG. 2 illustrates a top view of wire retainer 102 of FIG. 1 in an exemplary embodiment. In this view, groove 104 includes an inner diameter 108 and an outer diameter 109, which forms a width 110 of groove 104. Width 110 may be selected to be approximately the same as a width of ferromagnetic wire 106 to secure ferromagnetic wire 106 in place. A circumference 202 of groove 104 lies between inner diameter 108 of groove 104 and outer diameter 109 of groove 104. In FIG. 2, circumference 202 is illustrated to lie between inner diameter 108 of groove 104 and outer diameter 109 of groove 104, although circumference 202 may be reduced (e.g., circumference 202 may be about the same as a circle formed by inner diameter 108) or may be increased (e.g., circumference 202 may be about the same as a circle formed by outer diameter 109).

In FIG. 1, groove 104 is located on a surface of wire retainer 102 that is away from magnetic field generator 112, although in other embodiments groove 104 may be fabricated to be on the opposite side. Magnetic field generator 112 in this embodiment includes any system, component, or device that is capable of generating a magnetic field. Some examples of magnetic field generator 112 include permanent magnets and electromagnets. Permanent magnets may include magnetic metallic elements (e.g., Iron, Cobalt, and Nickel), composite materials (e.g., Iron and ceramics), and rare-earth magnets (e.g., lanthanide elements). Electromagnets typically include a current carrying coil wrapped around a ferromagnetic material such as Iron, Cobalt, Nickel, or their alloys. The current carrying coil may include a plurality of loops of wire and/or a bundle of individual loops of wire.

Magnetic field generator 112 is able to provide a substantially homogeneous magnetic field 114 along circumference 202 of groove 104. This ensures that ferromagnetic wire 106 is not subjected to a magnetic field strength that varies substantially from one portion of groove 104 to the other. For example, the field strength (B) in Tesla of magnetic field 114 as illustrated in FIG. 2 may be similar within groove 104 (e.g., at the same height 118 within groove 104) regardless of the particular location along groove 104. In some embodiments, magnetic field generator 112 may be positioned along the same centerline 116 as circumference used to form groove 104 to ensure that the field strength is similar along groove 104.

Although the field strength B may be similar, a field gradient still exists across ferromagnetic wire 106. The field gradient is generated by the geometry of magnetic field generator 112.

The magnetic field gradient imposed on ferromagnetic wire 106 generates an attractive force between magnetic field generator 112 and ferromagnetic wire 106, which is sensed by a force sensor 120. Force sensor 120 includes any system, component, or device that is capable of determining the attractive force generated between magnetic field generator 112 and ferromagnetic wire 106. Force sensor 120 is coupled with magnetic field generator 112 (e.g., by a non-magnetic pedestal 122 in some embodiments), which allows force sensor 120 to determine the attractive force between magnetic field generator 112 and ferromagnetic wire 106. For instance, if force sensor 120 is a balance or some other type of weight measuring system (e.g., a force balance), then the attractive force may be determined by zeroing out the weight (or drag, if system 100 is inverted) of magnetic field generator 112 (and pedestal 122, if present) prior to placing ferromagnetic wire 106 in groove 104 of wire retainer 102.

Generally, the attractive force is based on the magnetic permeability of ferromagnetic wire 106, with differences in the magnetic permeability from one sample of ferromagnetic wire 106 to another translating to different attractive forces being generated. In some cases, the measured attractive force may be used to explicitly calculate the magnetic permeability of ferromagnetic wire 106 if certain variables are either calculated or known. For example, the equation $F=\mu \cdot B \cdot dB/dz \cdot V$ may be used to when measuring the force (F) in the z direction (e.g., vertically in FIG. 1) utilizing force sensor 120, solving for $\mu$. In this equation, B is the strength of magnetic field 114 within groove 104, which may be calculated or measured. dB/dz is the magnetic field gradient in the z direction, which may be calculated or measured. V is the volume of ferromagnetic wire 106.

In other cases, the attractive force may be used to represent the magnetic permeability of ferromagnetic wire 106 if system 100 is calibrated with a wire having a known magnetic permeability. For instance, if a wire of known magnetic permeability is placed in wire retainer 102 and the force measured, other samples of ferromagnetic wires that are tested that have a similar force measurement will have a magnetic permeability that is similar to the calibration wire. Thus, it is not always necessary that B and dB/dz be calculated or measured in order for system 100 to provide information regarding the magnetic permeability of ferromagnetic wire 106.

Figure 3:
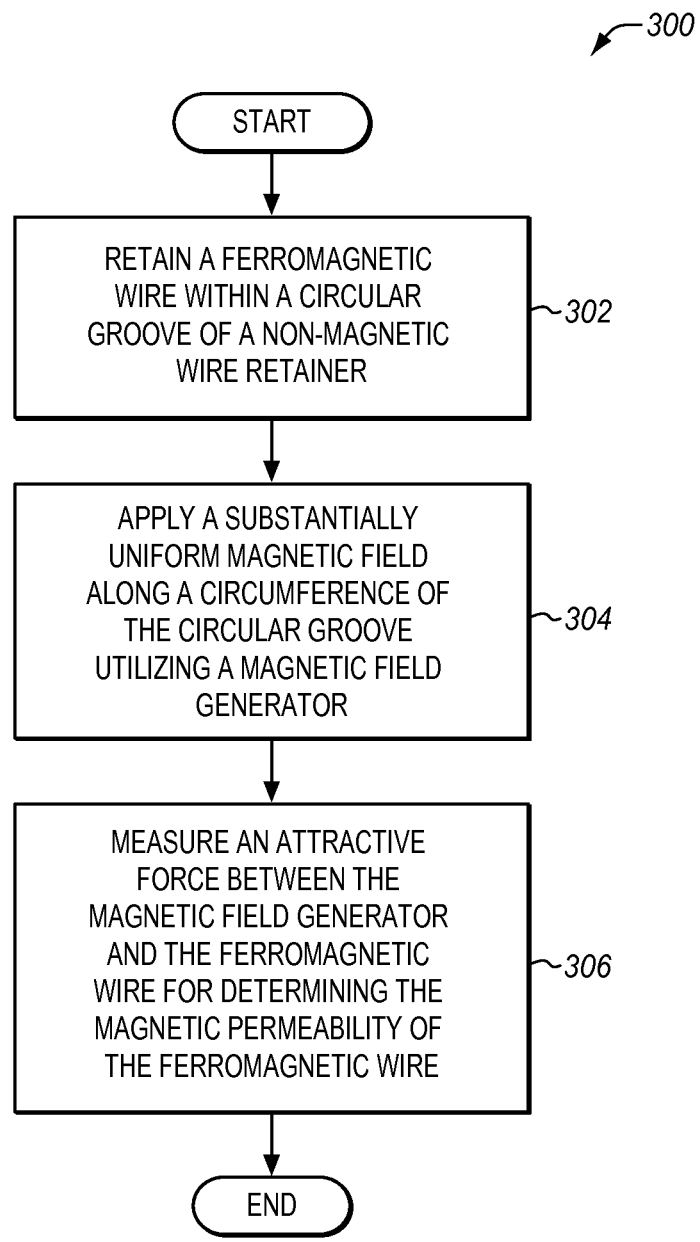
FIG. 3 is a flow chart of a method for measuring a magnetic permeability of a ferromagnetic wire in an exemplary embodiment.

FIG. 3 is a flow chart of a method 300 for measuring a magnetic permeability of a ferromagnetic wire in an exemplary embodiment. The steps of method 300 will be described with respect to FIGS. 1-2; although one skilled in the art will understand that method 300 may be performed by other devices or systems not shown. The steps of method 300 are not all inclusive and may include other steps not shown. Further, the steps may be performed in an alternate order.

In step 302, ferromagnetic wire 106 is retained within groove 104 of wire retainer 102. For instance, a spool of ferromagnetic wire may be received from a manufacturer, and testing a sample of the wire may be desired prior to allowing the wire to be fabricated into a product, such as an induction heating blanket. In some cases, small changes in the manufacturing process of the wire can drastically change the magnetic permeability of the wire, which can affect the thermal performance of thermal blankets that are fabricated with the wire.

In step 304, a magnetic field 114 is applied along circumference 202 of groove 104 utilizing magnetic field generator 112. Magnetic field 114 is applied substantially uniformly such that it does not vary by more than a threshold amount. The magnetic field gradient at ferromagnetic wire 106 generates an attractive force between ferromagnetic wire 106 and magnetic field generator 112. In step 306, the attractive force is measured (e.g., by force sensor 120) for determining the magnetic permeability of ferromagnetic wire 106. For example, the force may be used as part of the calculation of the magnetic permeability of ferromagnetic wire 106 (e.g., utilizing $F=\mu \cdot B \cdot dB/dz \cdot V$ or an equivalent equation), or the force may be used as a proxy for the magnetic permeability (e.g., by comparing the force to a reference force generated by a measuring a wire having a known magnetic permeability). In either case, system 100 and method 300 allows for the magnetic permeability of ferromagnetic wire 106 to be quickly and easily determined or inferred.

In some embodiments, a heat source 124 (e.g., an infrared heat source) may be used to heat ferromagnetic wire 106 to different temperatures, while system 100 is used to measure changes in the magnetic permeability of ferromagnetic wire 106. This allows system 100 to identify a temperature dependent relationship of the magnetic permeability of ferromagnetic wire 106. For instance, it may be desirable that the magnetic permeability of ferromagnetic wire 106 falls rapidly at a particular temperature. This reduces the self-heating of the wire when a target temperature is reached. By measuring the magnetic permeability of ferromagnetic wire 106 at different temperatures, it can be verified that the magnetic permeability does indeed change as expected at or near the target temperature.

Figure 4:
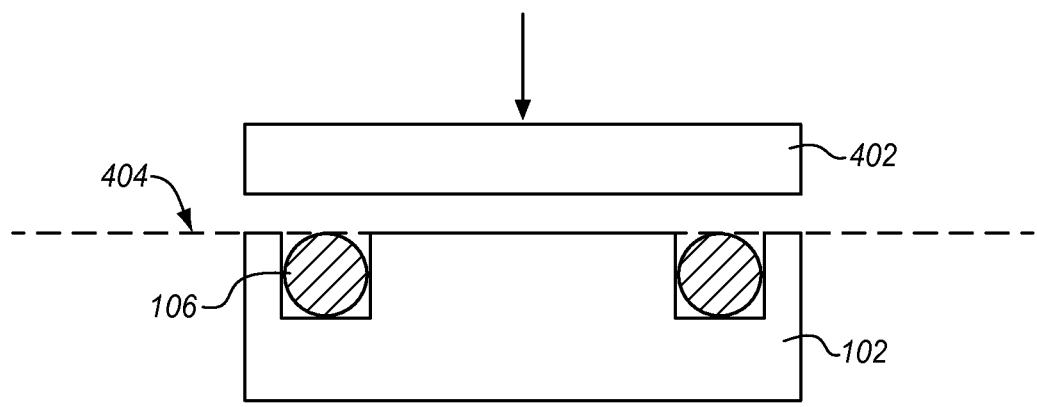
FIG. 4 illustrates a cross-sectional view of the wire retainer of FIG. 1 in an exemplary embodiment.

In some embodiments, a non-magnetic retaining plate is used to secure ferromagnetic wire 106 within circular groove 104. FIG. 4 illustrates a cross-sectional view of wire retainer 102 in an exemplary embodiment. In this view, a non-magnetic retaining plate 402 is used to secure ferromagnetic wire 106 within grove 104. Retaining plate 402 is clamped to a surface 404 of wire retainer 102 that includes groove 104, which securely fixes ferromagnetic wire 106 within groove 104. This ensures that ferromagnetic wire 106 lies flat within groove 104, which may improve the measurement of the magnetic permeability of ferromagnetic wire 106.

Figure 5:
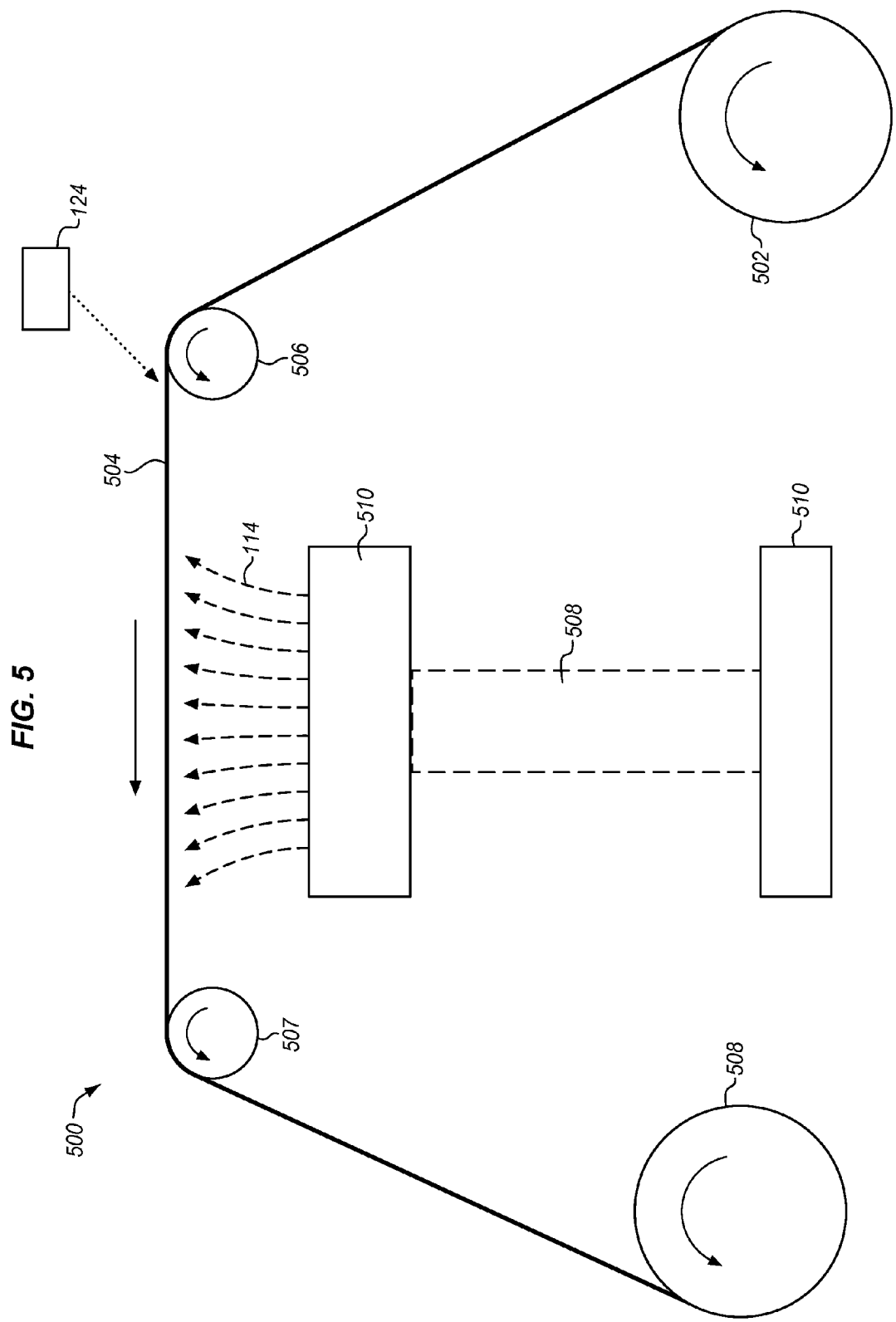
FIG. 5 illustrates a system for in-line measurement of changes in a magnetic permeability along a length of ferromagnetic wire in an exemplary embodiment.

In some cases, it may be desirable to identify changes in the magnetic permeability of ferromagnetic wire 106 using an in-line measurement. For example, rather than measuring a small sample of ferromagnetic wire 106 from a spool of wire, it may be desirable to quickly determine if the magnetic permeability is changing over a length of ferromagnetic wire 106. FIG. 5 illustrates a system 500 for in-line measurement of changes in a magnetic permeability along a length of ferromagnetic wire in an exemplary embodiment.

In this embodiment, a spool 502 holds a length of ferromagnetic wire 504, which will be applied to system 500 for testing. System 500 includes a first roller 506, which directs ferromagnetic wire 504 under tension to a second roller 507. Roller 507 directs ferromagnetic wire 504 to a take-up spool 508. System 500 includes a magnetic field generator 510 (e.g., a permanent magnet, an electromagnet, etc.), which applies a magnetic field 114 to ferromagnetic wire 504. Ferromagnetic wire 504 travels past magnetic field generator 510 in the direction of the arrow in FIG. 5. A force sensor 512 (e.g., a force balance) is coupled to magnetic field generator 510 (e.g., via non-magnetic pedestal 514), and is able to measure the attractive force generated between ferromagnetic wire 504 and magnetic field generator 510. This attractive force may change over time as ferromagnetic wire 504 travels past magnetic field generator 510, which indicates possible changes to the magnetic permeability of ferromagnetic wire 504.

Although magnetic field 114 may not be homogeneously applied to ferromagnetic wire 504, changes in the attractive force generated between ferromagnetic wire 504 and magnetic field generator 510 represent changes in the magnetic permeability of ferromagnetic wire 504 over some length. For instance, a decreasing force over the length of ferromagnetic wire 504 may indicate that the magnetic permeability of ferromagnetic wire 504 is non-uniform, which may not be desirable. Or, an increasing force over the length of ferromagnetic wire 504 may indicate that the magnetic permeability of ferromagnetic wire 504 is non-uniform, which also may not be desirable. If it is determined that the magnetic permeability of ferromagnetic wire 504 is changing across the length of ferromagnetic wire 504, then it may be desirable to obtain a small sample of ferromagnetic wire 504 for further testing. For instance, a number of samples of ferromagnetic wire 504 may be obtained over the length of ferromagnetic wire 504, and system 100 (see FIG. 1) may be used to determine if the magnetic permeability of the samples are within a range of acceptable values for ferromagnetic wire 504.

Utilizing system 500, in-line measurements can quickly identify if further testing of ferromagnetic wire 504 may be desirable to ensure that the magnetic permeability of ferromagnetic wire 504 lies within a range of acceptable values.

In some embodiments, a heat source 124 (e.g., an infra-red heat source) may be used to heat ferromagnetic wire 504 to a target temperature to determine how the magnetic permeability of ferromagnetic wire 504 varies along the length at the target temperature. For instance, if it is desirable that the magnetic permeability of ferromagnetic wire 504 at 350 degrees Celsius is close to a particular target value, then heat source 124 may be used to heat ferromagnetic wire 504 to 350 degrees Celsius while measuring the attractive forces generated between ferromagnetic wire 504 and magnetic field generator 510. System 500 may include additional components, not shown, to ensure that ferromagnetic wire 504 between rollers 506-507 is maintained at the target temperature, including temperature sensors, thermal shields placed proximate to ferromagnetic wire 504 between rollers 506-507, etc.

Figure 7A:
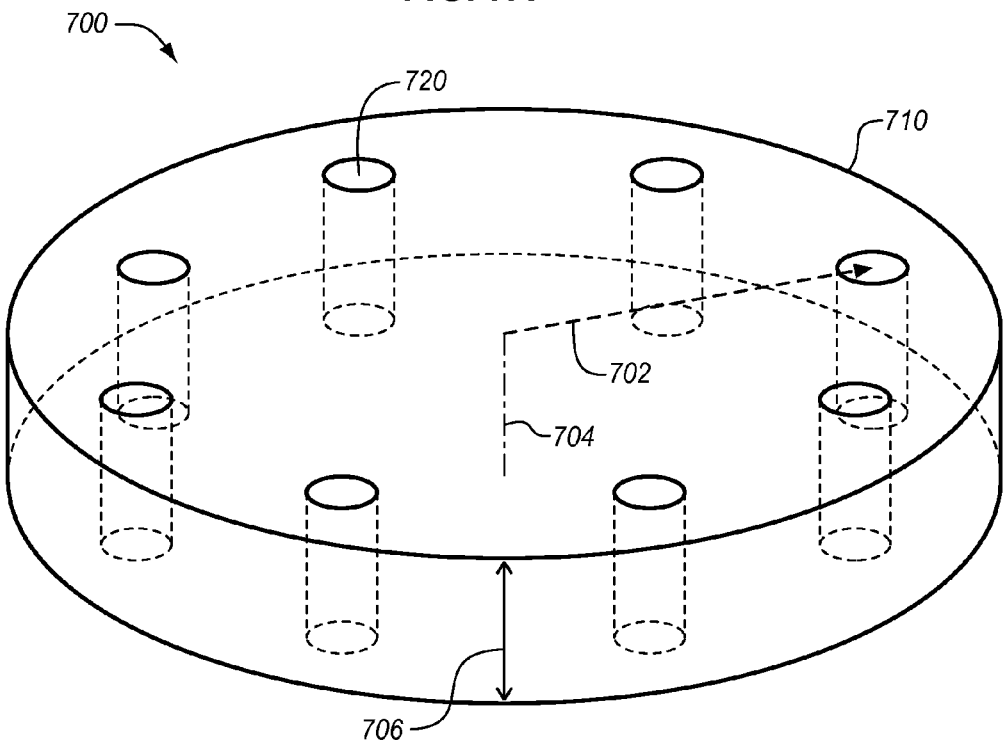
FIG. 7A illustrates an isometric view of another wire retainer in an exemplary embodiment.

FIG. 7A illustrates an isometric view of another wire retainer 700 in an exemplary embodiment. In this embodiment, wire retainer 700 includes a cylindrical disk 710 that is configured with holes 720 that are formed at a radius 702 from an axis 704 of disk 710. Disk 701 is formed from a non-magnetic material that may be similar to wire retainer 102 of FIG. 1. A thickness 706 of disk 710 may be varied to alter the depth of holes 720 within disk 710.

Figure 7B:
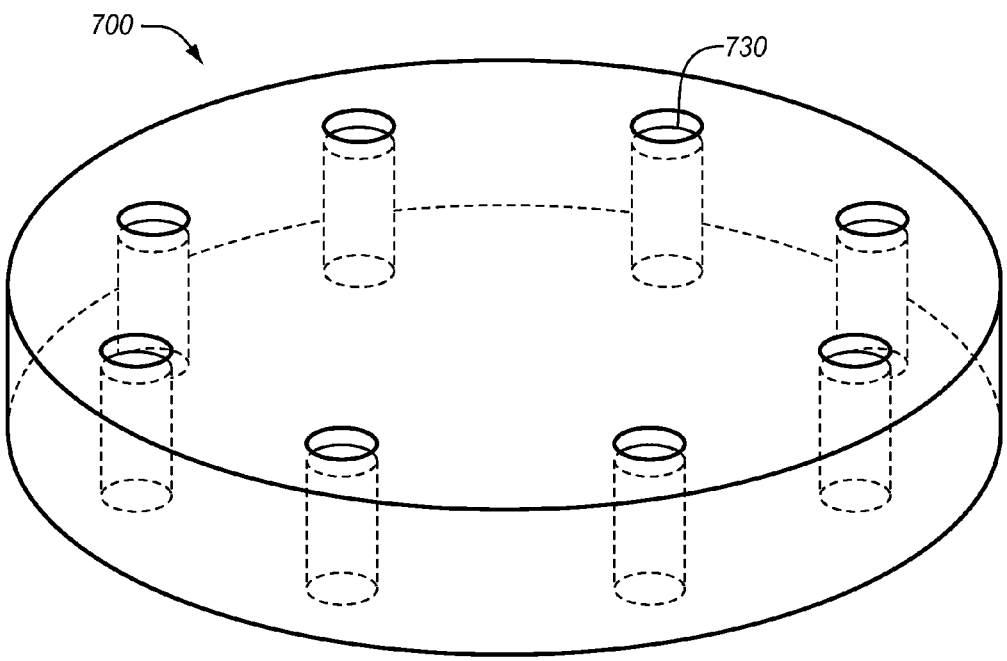
FIG. 7B illustrates an isometric view of the wire retainer of FIG. 7A loaded with ferromagnetic wire in an exemplary embodiment.

FIG. 7B illustrates an isometric view of the wire retainer of FIG. 7A loaded with ferromagnetic wire 730 in an exemplary embodiment. Wires 730 are placed in holes 720 during testing. The diameter of holes 720 is larger than the diameter of wires 730 for easy insertion and removal of wires 730. Although eight holes are illustrated in FIGS. 7A-7B, any number of holes 720 may be used. Further, wires 730 may be placed at different radii from the axis of disk 710.

One advantage of this embodiment is that wires 730 are retained in a direction that is substantially similar to the direction of the magnetic field lines emanating from a permanent magnet (not shown in FIGS. 7A-7B, which is how they may be typically used in induction heating applications. This geometry also aids in the magnetization of the wires. The wires experience a larger magnetic field gradient, so that the force on them is larger. This results in a smaller quantity of wire being used to perform a measurement of sufficient accuracy.

Example

The following example will be discussed with respect to system 600 for measuring the magnetic permeability of a ferromagnetic wire 106. System 600 in this embodiment includes wire retainer 102, which is located on a non-magnetic support assembly 602. Support assembly 602 positions the bottom of groove 104 in wire retainer 102 at a distance D from magnet 604. The distance D may be changed as desired to increase or decrease the magnetic field strength at ferromagnetic wire 106 that is generated by magnetic field 608 of magnet 604.

In this embodiment, magnet 604 is located on a measurement platform of a force balance 606. The weight of magnet 604 on force balance 602 may be calibrated out prior to placing a sample of ferromagnetic wire 106 in wire retainer 102. This allows force balance 606 to be read directly to determine the attractive force F generated between magnet 604 and ferromagnetic wire 106 without having to subtract out the weight of magnet 604.

Figure 6:
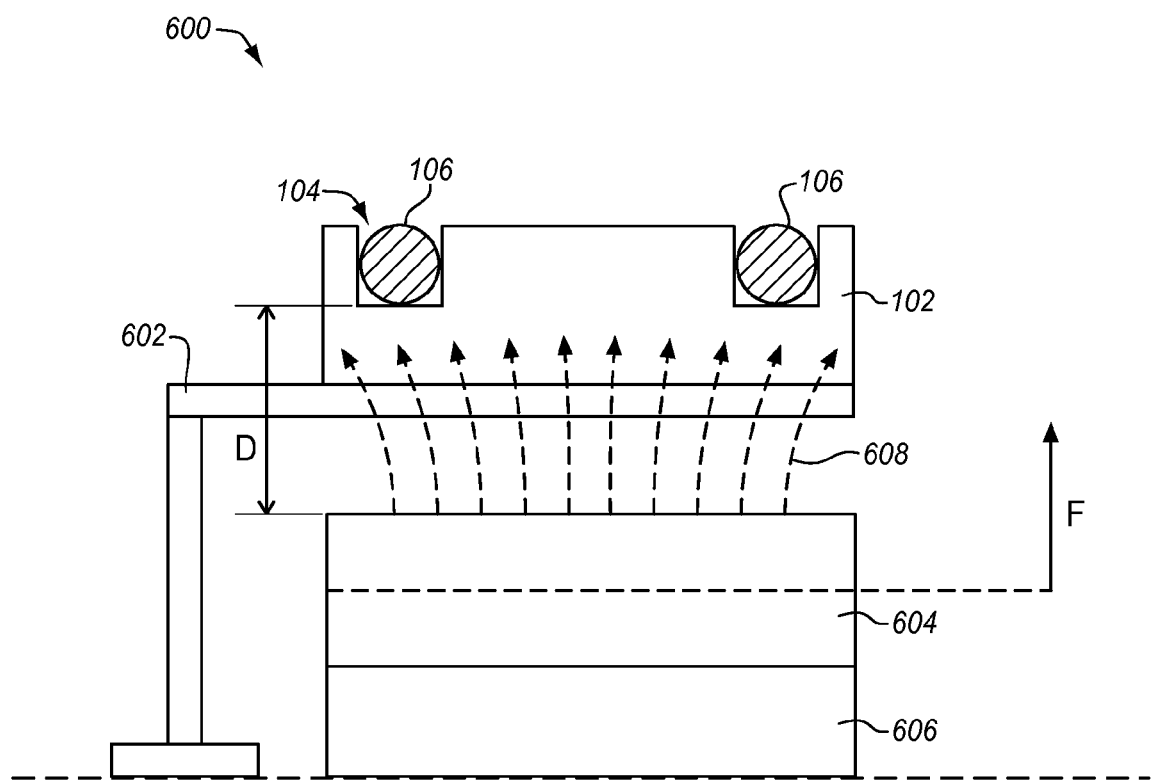
FIG. 6 illustrates another system for measuring a magnetic permeability of a ferromagnetic wire in an exemplary embodiment.

For the example, assume that the length of ferromagnetic wire 106 is $7.62 \times 10^{-2}$ meters (m) and the width is $0.254 \times 10^{-4}$ m. In this case, the volume of ferromagnetic wire 106 would be $3.85 \times 10^{-9}$ m$^3$. Ferromagnetic wire 106 is placed in wire retainer 102, and the attractive force F between ferromagnetic wire 106 and magnet 604 is measured by force balance 608 to be $1.9 \times 10^{-4}$ Newtons (N). Using the equation $F = \mu \cdot B \cdot dB/dz \cdot V$ and solving for $\mu$, the equation becomes $\mu = F/(B \cdot dB/dz \cdot V)$. The magnetic field strength B at ferromagnetic wire 106 is measured or calculated at $2.5 \times 10^{-3}$ Tesla (T), and the magnetic field gradient dB/dz in the z direction (vertical in FIG. 6) is measured or calculated at $2.5 \times 10^{-1}$ T/m. $\mu = F/(B \cdot dB/dz \cdot V)$, which is $1.9 \times 10^{-4}$ N/($2.5 \times 10^{-3} \cdot 0.2.5 \times 10^{-1}$ T/m $\cdot 7.62 \times 10^{-2}$ m), or about $1.26 \times 10^{-4}$ H/m.

Although specific embodiments were described herein, the scope is not limited to those specific embodiments. Rather, the scope is defined by the following claims and any equivalents thereof.

The invention claimed is:

1. An apparatus for measuring a magnetic permeability of a ferromagnetic wire, the apparatus comprising:
   a non-magnetic wire retainer having a circular groove that is configured to retain the ferromagnetic wire for measurement;
   a permanent magnet that is proximate to the non-magnetic wire retainer that is configured to provide a substantially uniform magnetic field along a circumference of the circular groove, wherein the permanent magnet is positioned proximate to the non-magnetic wire retainer such that a centerline of the permanent magnet is equidistant from the circumference of the circular groove to provide the substantially uniform magnetic field along the circumference of the circular groove; and
   a force sensor coupled to the permanent magnet that is configured to measure an attractive force between the permanent magnet and the ferromagnetic wire for determining the magnetic permeability of the ferromagnetic wire.

2. The apparatus of claim 1 further comprising:
   a non-magnetic retaining plate that is configured to clamp to the non-magnetic wire retainer along a surface of the non-magnetic wire retainer that includes the circular groove to retain the ferromagnetic wire within the circular groove.

3. The apparatus of claim 1 further comprising:
   a non-magnetic pedestal that mechanically couples the force sensor to the permanent magnet.

4. The apparatus of claim 1 wherein:
   the force sensor comprises a force balance.

5. The apparatus of claim 1 further comprising:
   a heat source configured to heat the ferromagnetic wire within the circular groove to a target temperature;
   wherein the force sensor is configured to measure a first attractive force between the permanent magnet and the ferromagnetic wire at a first temperature, to measure a second attractive force between the permanent magnet and the ferromagnetic wire at the target temperature, and to determine a temperature dependence of the magnetic permeability of the ferromagnetic wire based on a difference between the first attractive force and the second attractive force.

6. The apparatus of claim 1 further comprising:
a heat source configured to heat the ferromagnetic wire within the circular groove to a target temperature for determining the magnetic permeability of the ferromagnetic wire at the target temperature.

7. A method for measuring a magnetic permeability of a ferromagnetic wire, the method comprising:
retaining the ferromagnetic wire within a circular groove of a non-magnetic wire retainer;
applying a substantially uniform magnetic field along a circumference of the circular groove utilizing a permanent magnet by positioning the permanent magnet proximate to the non-magnetic wire retainer such that a centerline of the permanent magnet is equidistant from the circumference of the circular groove to provide the substantially uniform magnetic field along the circumference of the circular groove; and
measuring an attractive force between the permanent magnet and the ferromagnetic wire for determining the magnetic permeability of the ferromagnetic wire.

8. The method of claim 7 wherein retaining the ferromagnetic wire further comprises:
clamping a non-magnetic retaining plate to the non-magnetic wire retainer along a surface of the non-magnetic wire retainer that includes the circular groove to retain the ferromagnetic wire within the circular groove.

9. The method of claim 7 wherein measuring the attractive force further comprises:
measuring the attractive force utilizing a force sensor coupled to the permanent magnet.

10. The method of claim 7 further comprising:
measuring a first attractive force between the permanent magnet and the ferromagnetic wire at a first temperature;
heating the ferromagnetic wire within the circular groove to a target temperature;
measuring a second attractive force between the permanent magnet and the ferromagnetic wire at the target temperature; and
determining a temperature dependence of the magnetic permeability of the ferromagnetic wire based on a difference between the first attractive force and the second attractive force.

* * * * *